United States Patent [19]
Shipp

[11] Patent Number: 5,792,138
[45] Date of Patent: Aug. 11, 1998

[54] CORDLESS BIPOLAR ELECTROCAUTERY UNIT WITH AUTOMATIC POWER CONTROL

[75] Inventor: John I. Shipp, Tullahoma, Tenn.

[73] Assignee: Apollo Camera, LLC, Tullahoma, Tenn.

[21] Appl. No.: 604,850

[22] Filed: Feb. 22, 1996

[51] Int. Cl.$^6$ ................................................. A61B 17/39
[52] U.S. Cl. .............................. 606/38; 606/34; 606/48; 606/50; 429/61
[58] Field of Search ....................... 606/34, 37–40, 606/48, 50, 51; 429/61

[56] References Cited

U.S. PATENT DOCUMENTS

| | | | |
|---|---|---|---|
| 2,894,512 | 7/1959 | Tapper | 128/303 |
| 2,994,324 | 8/1961 | Lemos | 128/303 |
| 3,646,931 | 3/1972 | Phelps et al. | 128/2.05 |
| 3,807,411 | 4/1974 | Harris et al. | 128/419 |
| 3,978,312 | 8/1976 | Burton et al. | 219/240 |
| 4,034,762 | 7/1977 | Cosens et al. | 128/303.17 |
| 4,276,883 | 7/1981 | McDonald et al. | 128/419 |
| 4,357,943 | 11/1982 | Thompson et al. | 128/419 |
| 4,515,159 | 5/1985 | McDonald et al. | 128/419 |
| 4,658,818 | 4/1987 | Miller, Jr. et al. | 128/303.1 |
| 4,674,499 | 6/1987 | Pao | 128/303.14 |
| 4,805,616 | 2/1989 | Pao | 128/303.17 |
| 4,827,906 | 5/1989 | Robicsek et al. | 600/17 |
| 4,878,493 | 11/1989 | Pasternak et al. | 128/303 |
| 5,025,811 | 6/1991 | Dobrogowski et al. | 128/898 |
| 5,167,660 | 12/1992 | Altendorf | 606/40 |
| 5,269,780 | 12/1993 | Roos | 606/42 |
| 5,368,041 | 11/1994 | Shambroom | 128/731 |
| 5,376,088 | 12/1994 | Glaros | 606/51 |
| 5,422,567 | 6/1995 | Matsunaga | 606/38 |
| 5,608,306 | 3/1997 | Rybeck et al. | 429/61 |

FOREIGN PATENT DOCUMENTS

| | | | |
|---|---|---|---|
| 2133290 | 7/1984 | United Kingdom | 606/37 |

Primary Examiner—Lee S. Cohen
Attorney, Agent, or Firm—Waddey & Patterson; Mark J. Patterson

[57] ABSTRACT

A cordless electrocautery unit for use in surgical procedures is described in which the unit is battery operated and therefore cordless. The unit is microprocessor controlled and provides for automatic feedback and control of the output power, in accordance with one of multiple power levels selected by the user.

9 Claims, 6 Drawing Sheets

CORDLESS BIPOLAR ELECTROCAUTERY UNIT WITH AUTOMATIC POWER CONTROL

BACKGROUND OF THE INVENTION

Electrocautery has been used in surgical procedures for many years for sealing openings in small veins and arteries, sealing certain other lumens such as in vasectomies procedures, and for cutting and removing tissue. Electrocautery has become of particular importance with the increased popularity of laparoscopic surgery because of the difficulty in tying sutures and using scalpels through small trocar ports.

In a typical laparoscopic procedure, such as a laparoscopic cholecystectomy, a monopolar electrocautery unit is used to separate the gall bladder from the liver bed and to cauterize bleeders. Prior art monopolar electrocautery units have a single internal electrode attached to the distal end of a long handle. The internal electrode is inserted into the abdominal cavity through a trocar. The handle is manipulated so that the electrode is positioned proximate the bleeder or other tissue of concern. When the unit is activated by the surgeon, radio frequency (RF) energy is generated external to the patient and transmitted from the internal electrode as an RF current. The current passes through the tissue to be cut or cauterized, traveling through the patients body, and returning to the cautery unit via a large flat external electrode in contact with the patients back. Cutting is accomplished because the high current density proximate the small internal electrode causes the water content of the adjacent tissue cells to evaporate, thereby bursting the cells. Cauterizing is accomplished by less power dissipation. Heating is localized near the internal electrode with little charring.

A number of problems can be associated with the use of monopolar cautery. If the patient's back does not make good contact with the external electrode, the current density at the point where the charge exits the body can be high, producing severe burns to the patient. Bipolar electrocautery, in which both electrodes are internal, solves this problem. The current density between the adjacent electrodes, both of which are put in contact with the tissue to be cut or cauterized, is readily controlled because the return path of the RF current is only from one electrode to another, usually spaced less than a millimeter apart. U.S. Pat. Nos. 4,034,762; 4,674,499; 4,805,616; and 5,269,780 describe such bipolar probes for various surgical applications.

However, further problems arise from the use of prior art bipolar electrocautery devices, related to their portability and reliance on conventional AC power sources. Faulty components or poor electrical isolation can create a current leak from the AC power source to the cutting electrodes, causing severe injury or even death. Cosens, in U.S. Pat. No. 4,034,762, describes a battery-operated bipolar electrocautery unit, designed for use in vasectomy procedures. The '762 device generates RF energy using a multi-vibrator and a step-up transformer. Although the '762 unit solves the problems of portability and AC leakage, it is inefficient and requires a larger battery than could otherwise be used. Also, the '762 unit has no convenient means for adjusting the power delivered to the tissue and cannot control the amount of power delivered to the cutting area as the load resistance of the tissue changes during the cutting process.

What is needed, then, is an electrocautery unit which is portable, safe, usable in laparoscopic procedures, and which is capable of operating at automatically controlled power levels selectable by the user, even as the load resistance may change during use.

SUMMARY OF THE INVENTION

The electrocautery unit of this invention is cordless, as it relies on an integral, battery-powered regulated power supply. A microprocessor controls the operation of the electrocautery unit, and includes an input whereby the user of the unit can select one of multiple predetermined output power levels. An output on the microprocessor provides a pulse-width-modulated (PWM) drive signal to the input of a drive circuit. The output of the drive circuit is connected to the primary of a step-up transformer, with the secondary of the transformer connected to a conventional bipolar cautery probe.

The output voltage across the cautery electrodes and the output current flowing through the electrodes are monitored in real time by a feedback control circuit. Analog signals corresponding to the output voltage and current are digitized and used by the microprocessor to adjust the PWM drive signal so that the power output is substantially maintained at the predetermined level.

Preferably, the electrocautery unit of this invention will also include a battery pack having an encoder, with the microprocessor having a decoder. In this embodiment, the microprocessor interrogates the battery encoder to verify that the battery installed in the unit is appropriate for the application. If not, operation of the unit is disabled.

The electrocautery unit of this invention also includes a digital display so that the user can visually confirm the power level selected.

DESCRIPTION OF THE PREFERRED EMBODIMENT

Figure 1:
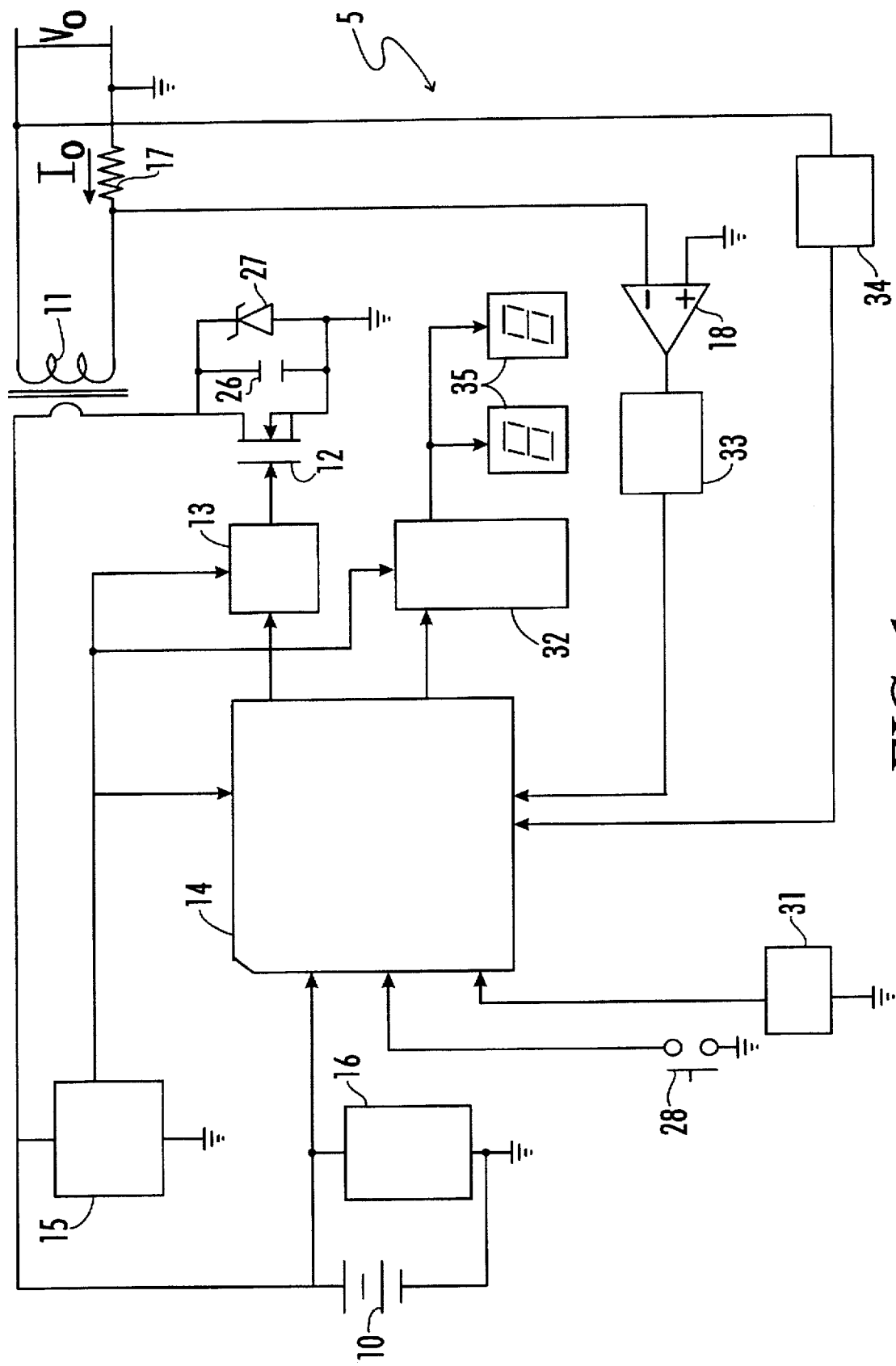
FIG. 1 is a block diagram of the cordless electrocautery unit of the present invention.
Figure 2A:
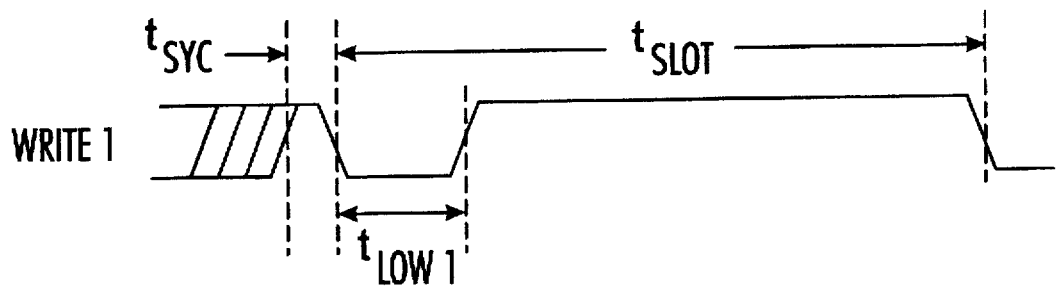
FIGS. 2a and 2b are graphical representations of the signal levels and signal timing associated with the communication of control signals from the battery decoder to the battery pack encoder in a preferred embodiment of the unit of FIG. 1, where $t_{syc}$ represents the synchronization signal, $t_{low1}$ represents the low logic signal for a write 1 time slot, $t_{low0}$ represents the low logic signal for a write 0 time slot, and $t_{slot}$ represents the duration of a single write time slot.
Figure 2B:
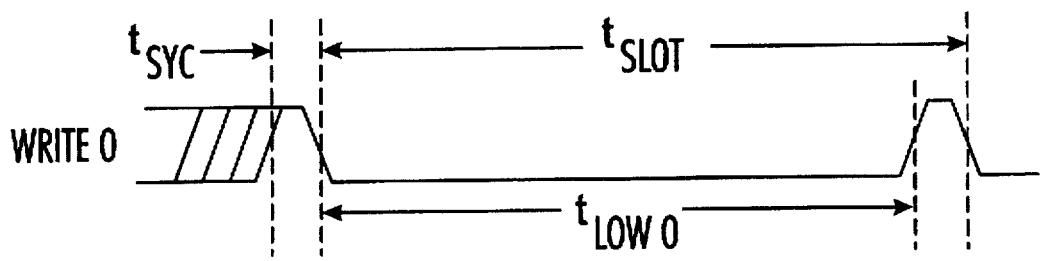
Figure 3A:
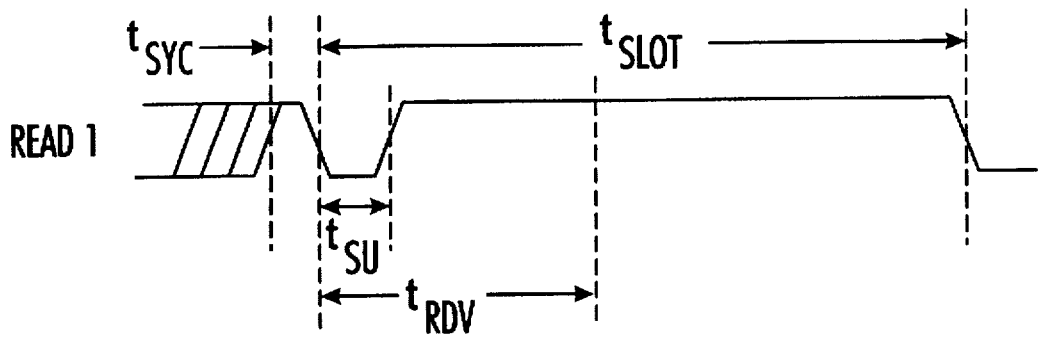
FIGS. 3a and 3b are graphical representations of the signal levels and signal timing associated with communication of battery identification data from the battery pack encoder to the cautery unit decoder, where $t_{syc}$ represents the synchronization signal, $T_{SU}$ represents the read data setup signal, $t_{RDV}$ represents the read data valid signal, and $t_{slot}$ represents the duration of a single read time slot.
Figure 3B:
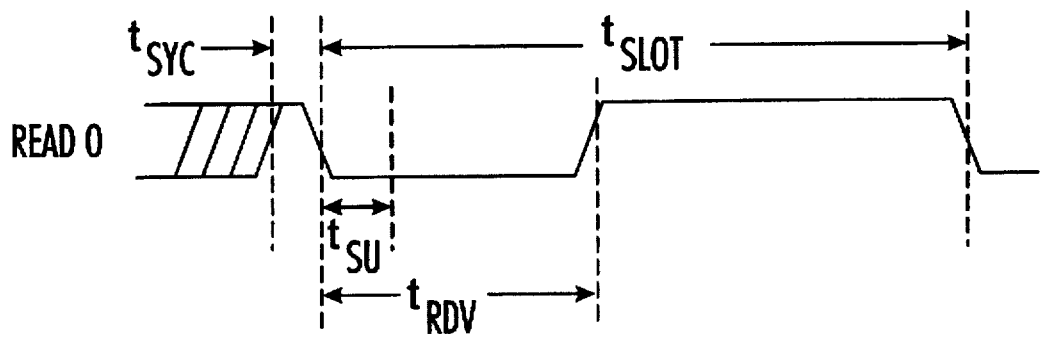
Figure 7A:
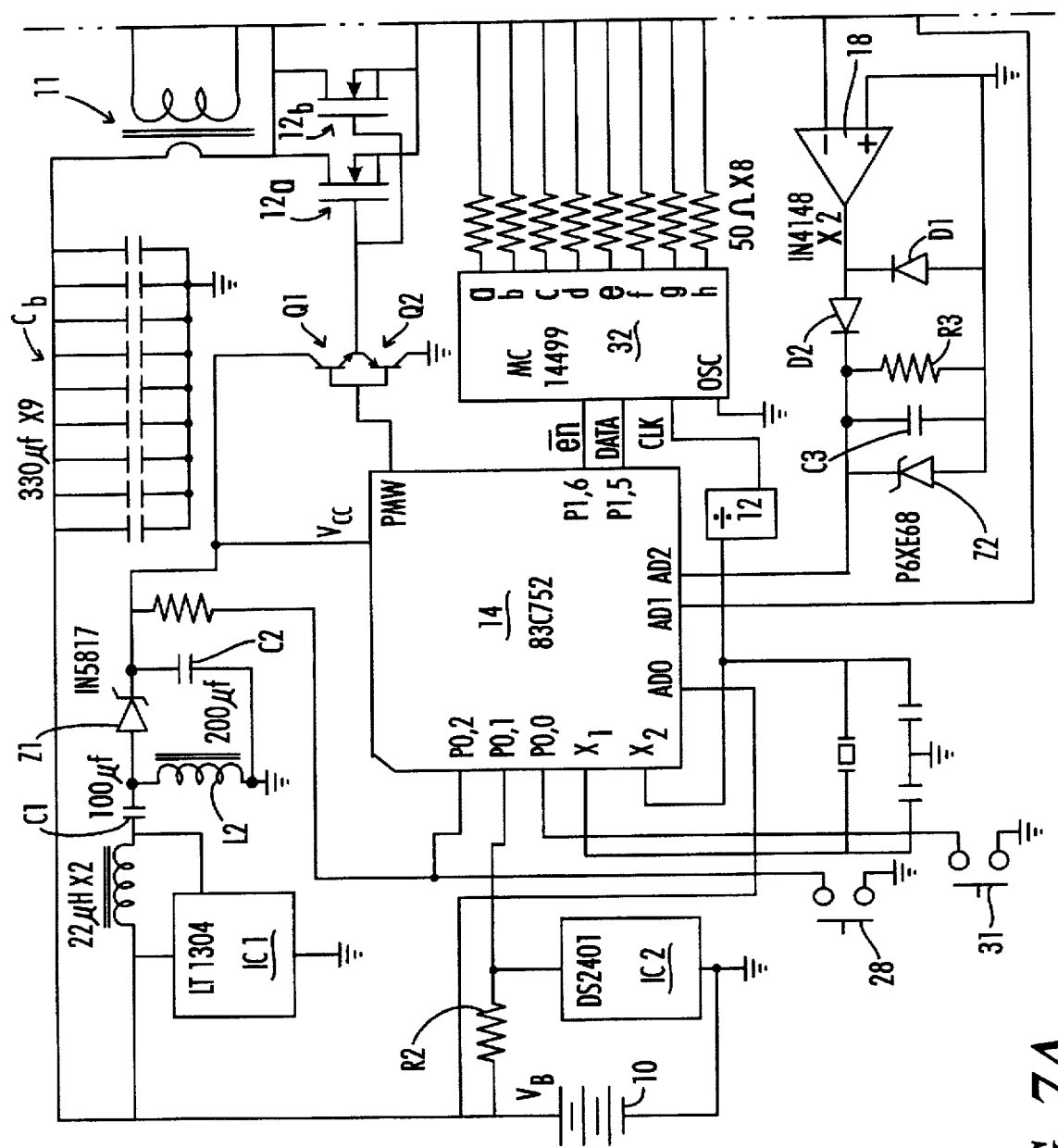
FIG. 7 is a schematic diagram of the cordless electrocautery unit of FIG. 1.
Figure 7B:
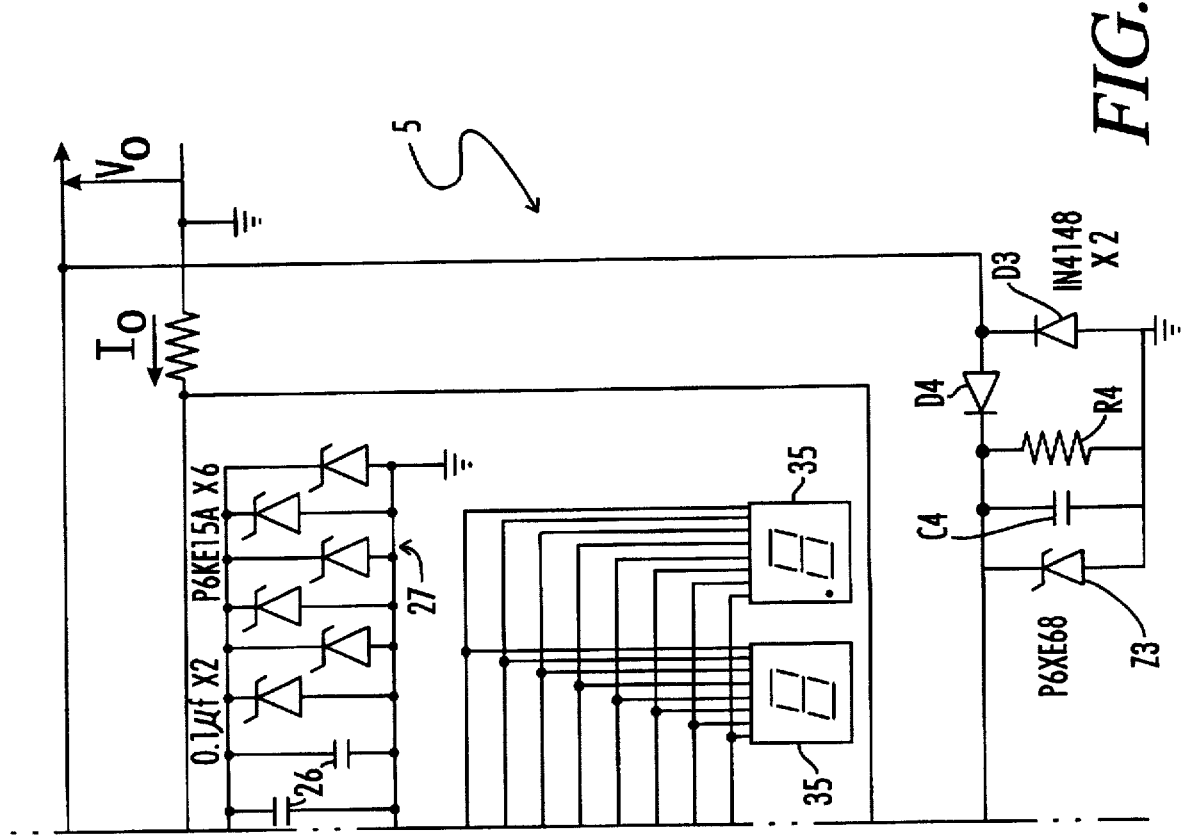

The general arrangement and a preferred embodiment of the electronic portion of a cordless electrocautery unit 5 are shown in FIGS. 1 and 7. The purpose of the unit is to generate a cautery output signal including an output voltage $V_{out}$ at the secondary of a step-up transformer 11. The cautery output signal $V_{out}$ represents an AC signal at a typical frequency of 400 kHz, and with typical peak voltages of 1200 volts, which is delivered to a conventional bipolar cautery probe (not shown), such as that described in U.S. Pat. No. 5,269,780. Application of $V_{out}$ across the electrodes of the probe creates a heat generating RF current ($I_{out}$) through tissue located between the electrodes.

The cautery unit 5 is portable and cordless, being powered by an internal battery 10. A single-cell 3 volt lithium sulfur dioxide battery can be used, having a sufficiently low internal impedance to deliver a cauterizing output power required by the needs of the surgeon, preferably variable up to 50 watts. The raw battery voltage $V_b$ is boosted in a switching regulator circuit 15, based on a switching regulator chip IC1, such as a type LT1304 from Linear Technology. Chokes L1 and L2, along with capacitors C1 and C2, and Zener diode Z1, smooth the output from IC1 to provide a 6.5 VDC regulated operating voltage $V_{cc}$ for the active components of the cautery unit 5, including a microprocessor 14, a drive circuit 13, a current sense amplifier 18, and a display decoder 32.

The cordless electrocautery unit 5 is improved over the battery-operated prior art because of its user selectable power output level. In accordance with this feature, an input switch 31 transmits a power level select signal to a power select input P0.0, preferably a memory register, in microprocessor 14. Preferably, the power level select signal will comprise one or more digital data pulses, with the number of pulses corresponding to discrete, user selected power levels. For example, the user may choose to use maximum (100%) power and upon making that selection by using input switch 31 (such as by depressing switch 31 ten times), ten pulses will be generated and stored for use in a temporary memory location in microprocessor 14. Or, if switch 31 is depressed only one time, one pulse will be generated and stored if only 10% power is selected. The power level selected will be displayed on a two digit LCD display 35. The display 35 is driven by a type MC14499 display decoder 32 through a bank of current limiting resistors $R_c$.

The power level of the cautery output signal $V_{out}$ is varied using pulse width modulation (PWM). Accordingly, microprocessor 14 generates a PWM digital signal at output PMW to the input of a driver circuit 13. Software resident in microprocessor 14 controls an internal data processor which causes the duty cycle (pulse width) of the drive signal to the input of drive circuit 13 to vary in proportion to the power level select signal previously stored in memory.

The drive circuit 13, shown in FIG. 7 as a pair of transistor Q1 and Q2 electrically connected in a "totem pole" configuration to switch a field effect transistor (FET) stage 12 (transistors 12a and 12b on FIG. 7), acts as a switch in series with the primary of output transformer 11. Thus, the battery voltage $V_b$ is switched on and off across the primary of transformer 11 at a rate and duty cycle determined by microprocessor 14, discharging the bank of capacitors $C_b$ (FIG. 7). Preferably, the switching frequency is approximately 400 kHz. The duty cycle is varied as described above, in accordance with the user determined power level select signal. The FET 12 is protected from transient voltages, and the peak voltage applied to the primary of transformer 11, by a one or more capacitors 26 and zener diodes 27.

The transformer 11 steps up the primary voltage to approximately 1200 volts peak. Consequently, the duty cycle of the PWM output of microprocessor 14 defines the power available to the primary of transformer 11, and hence to the transformer secondary and cautery probe (not shown) for delivery to the tissue. The power available at the probe is roughly proportional to the square root of the duty cycle.

The cautery unit 5 is activated when switch 28 is closed, which provides a power-on signal to an input of microprocessor 14, through resistor R1. However, in a preferred embodiment of the cautery unit, an encoder circuit 16, based on a digital serial number encoder IC2, is associated with battery 10. Encoder IC2, which preferably is integral to the package which includes battery 10, stores battery identification data and communicates that battery identification data on command to an input of microprocessor 14. A pull-up resistor R2 electrically connects encoder IC2 to the battery voltage $V_b$.

In a preferred embodiment of the cautery unit 5, the encoder chip IC2 can be a Model DS2401 Silicon Serial Number integrated circuit manufactured by Dallas Semiconductor. In such an embodiment, all data communications between encoder IC2 and microprocessor 14 is accomplished by a single interface line. Battery identification data stored in encoder IC2 can then include an eight-bit digitally encoded model or type number and a forty-eight bit battery identification code. Encoder IC2 in this embodiment can further include an eight-bit check value which can be used, as described below, to confirm that battery identification data from encoder IC2 has been correctly received by the system.

The data stored in encoder IC2 is accessed during read and write time slots, as shown on FIGS. 2a, 2b, 3a, and 3b.

Figure 6:
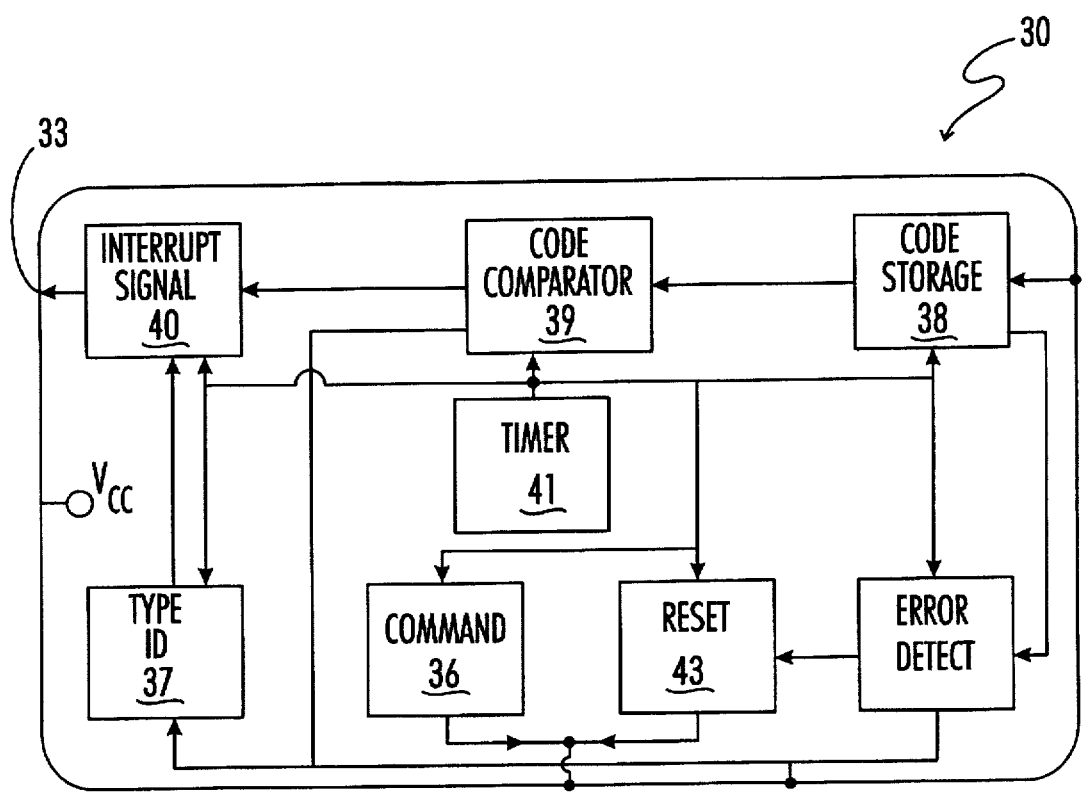
FIG. 6 is a block diagram of the decoder/controller section of the electrocautery unit of the present invention, as implemented in the microprocessor shown in FIGS. 1 and 7.

To fully implement in the electrocautery unit of the present invention all the features available from encoder IC2 as described above, a decoder/control unit 30 is illustrated in more detail in FIG. 6. Preferably, the decoder/control unit 30 is integral to microprocessor 14. A type 83C752 microprocessor from Phillips Electronics can be used in this application. A timer circuit 41 provides the various timing and logic signals in a conventional manner to other functional modules of decoder 30.

Figure 4:
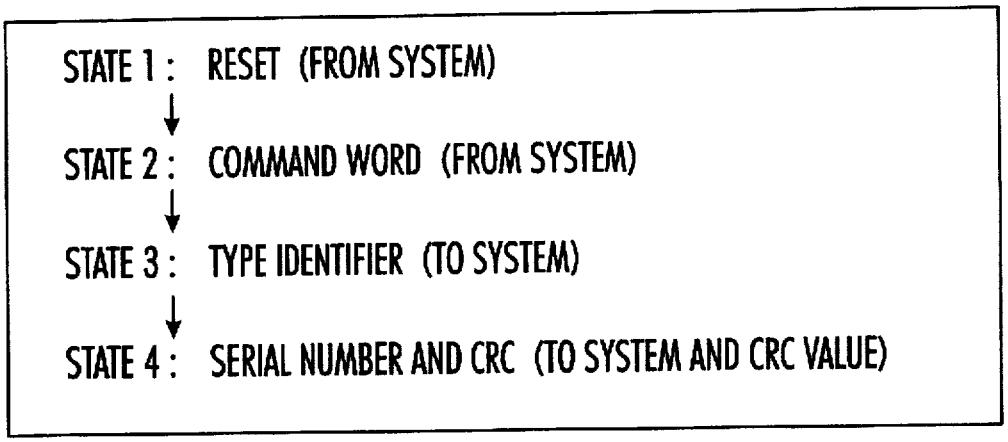
FIG. 4 is a table showing the sequence of states which are assumed by the battery encoder used in a preferred embodiment of the cautery unit.
Figure 5:
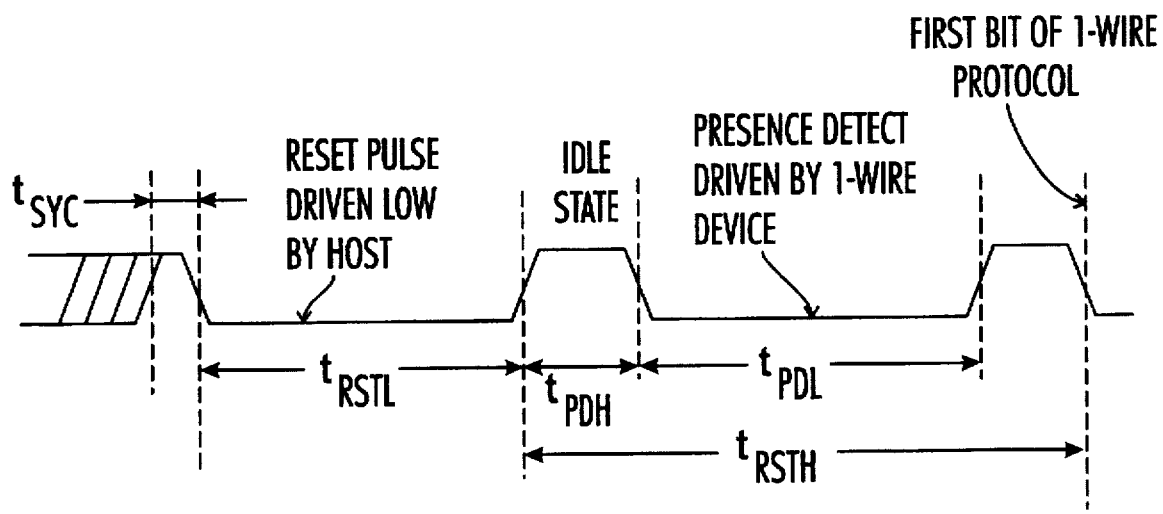
FIG. 5 represents the sequence and logic levels during generation of a reset pulse signal by the decoder and generation of presence detect signal by the battery encoder.

A reset pulse generator 43 is used to provide a control signal in the form of reset pulses to encoder IC2, as shown on FIG. 5. This allows encoder IC2 to progress in an organized sequence from an initial reset condition to a condition where it can receive control signals from decoder 30 and then communicate battery identification data, including the type number, the battery identification code, and the check value, such states of encoder IC2 being illustrated on FIG. 4. A command word generator 36 is also included in decoder 30 to generate other necessary control signals to encoder IC2.

When switch 28 is closed, a type number decoder/comparator module 37 receives the type number from encoder IC2 and makes the necessary comparisons to a pre-programmed type number stored in module 37 (non-volatile memory in microprocessor 14), which in the preferred embodiment is the hexadecimal number 01. Battery identification code comparator module 39, also part of decoder 30, receives the battery identification code from encoder IC2 and makes a comparison of the battery identification code to a unit identification code stored in unit code memory module 38. Code comparator module 39 also provides a comparison signal to interrupt signal generator 40 to indicate whether there has been a proper match of the battery identification code with the unit identification code. If the comparison signal from code comparator module 39 indicates a code mismatch, interrupt signal generator 40 then generates an interrupt signal, disabling operation of the electrocautery unit 5.

Thus, if the battery identification data from encoder IC2 is outside the allowable value, the microprocessor interrupts its PWM signal to the input of driver circuit 13, so that no cauterization signal $V_{out}$ is available at the probe. Under this interrupt condition, the battery 10 must be replaced before the unit 5 can be reset. Preferably, encoder circuit 16 will be integral to battery 10.

To further insure proper operation of the unit 5, an A/D input (AD0) of microprocessor 14 monitors the raw battery voltage $V_b$ and will shut the unit 5 down if the battery voltage goes too low.

In the improved electrocautery unit 5 of this invention, the power supplied to the cautery probe is monitored and controlled automatically by an automatic cautery power feedback and control circuit. The RF current $I_{out}$ which passes through the tissue being cauterized flows through a current sensing resistor 17. The value of current $I_{out}$ depends on the load (tissue) resistance as well as the amplitude of $V_{out}$ and is measured as a voltage drop across resistor 17. The voltage across resistor 17 is amplified by current sense differential amplifier 18 then rectified and filtered in a first rectifier/filter stage 33, which on FIG. 7 comprises diodes D1 and D2, capacitor C3, resistor R3, and Zener diode Z2. The output of rectifier/filter stage 33 is now an analog DC signal which is proportional to the magnitude of the current $I_{out}$ flowing through the tissue. This signal is digitized by an A/D converter integral to a analog input AD2 on microprocessor 14. The cautery output voltage $V_{out}$ is also rectified and filtered in a second rectifier/filter stage 34 (diodes D3 and D4, capacitor C4, resistor R4, and Zener diode Z3 on FIG. 7) and digitized at A/D converter input AD3 in microprocessor 14.

Thus, the product of the signals at inputs AD2 and AD3 is proportional to the cautery output power being supplied to the tissue. As the tissue impedance changes during the cauterizing or cutting process, a software sub-routine resident in microprocessor 14 adjusts the duty cycle of the PWM output signal to driver circuit 13, to maintain the selected power level pre-selected by the user. This output power feedback and control circuit also helps prevent injury or damage if the probe is inadvertently touched to other tools placed inside the body cavity.

Thus, although a particular embodiment of a new cordless electrocautery unit has been described, it is not intended that such description be construed as limiting the scope of this invention except as set forth in the following claims. Further, although certain components and operating parameters are described as being associated with the preferred embodiment, it is not intended that such be construed as limitations upon the scope of this invention except as set forth in the following claims.

What I claim is:

1. An electrocautery unit, including a cautery probe having bipolar electrodes, comprising:
   a. cautery signal generator means to generate a cautery output voltage and signal at a pre-determined cautery power output such that an RF current is caused to flow between the electrodes through tissue proximate the probe;
   b. power selection means to vary the pre-determined cautery power output in response to a power level selection made by a user of the unit such that the unit can be operated at multiple pre-determined cautery power output levels;
   c. a power supply, including a battery, integral to the unit and which is electrically connected to the cautery signal generator means such that the unit can be operated without an external power supply cord; and
   d. cautery power output feedback and control means to monitor the cautery output voltage and the RF current flowing through the tissue during operation of the unit and to adjust, in response to the magnitudes of the of output voltage and RF current, the magnitude of the cautery output signal such that the pre-determined cautery power output selected by the user is automatically maintained during operation of the unit.

2. The electrocautery unit of claim 1 wherein the battery includes an encoder containing electronic battery identification data, and the unit further comprising:
   a. means to electronically store unit identification data;
   b. means to compare the battery identification data to the unit identification data; and
   c. interrupt means to interrupt operation of the unit if the battery identification data does not match the unit identification data.

3. The electrocautery unit of claim 1 wherein the cautery signal generator means includes means to vary the cautery output signal by pulse width modulation in response to the power level selection means and in response to the cautery power output feedback and control means.

4. The electrocautery unit of claim 3 wherein the cautery power output feedback and control means comprises:
   a. means to produce a first digital signal proportional to the magnitude of the RF current;
   b. means to produce a second digital signal proportional to the magnitude of the cautery output voltage; and
   c. means to calculate the actual cautery power output from the first and second digital signals.

5. An electrocautery unit for cutting and heating tissue in conjunction with a bipolar cautery probe comprising:
   a. signal generator means to generate and supply a cautery output signal to the probe;
   b. automatic power output control means to control the cautery output signal such that a cautery output voltage magnitude and the magnitude of the current flowing through the tissue during use of the unit is monitored and adjusted during use to maintain a pre-determined power output level; and
   c. a battery integral to the unit and operatively connected to the signal generator means and to the power output control means to provide for cordless operation of the unit.

6. The electrocautery unit of claim 5 further comprising power output selection means to adjust the pre-determined power output level of the unit in response to a user selection.

7. The electrocautery unit of claim 6 further comprising means to display the predetermined power output level selected by the user.

8. An electrocautery unit for use with a bipolar cautery probe comprising:
   a. a microprocessor, including a signal generator connected to a cautery drive signal output, a first A/D converter input, and a second A/D converter input;
   b. an output transformer having a primary winding and a secondary winding;
   c. a drive circuit having a drive circuit input and a drive circuit output, the drive circuit input connected to the cautery drive signal output and the drive circuit output operatively connected to the primary winding of the output transformer;

d. an output current feedback circuit which provides an output current signal to the first A/D converter input of the microprocessor, the output current feedback signal corresponding to a magnitude of output current from the unit;

e. an output voltage feedback circuit electrically connecting the secondary winding of the output transformer and which provides an output voltage feedback signal to the second A/D converter input of the microprocessor corresponding a magnitude of the output voltage; and f. an integral battery connected to a regulated power supply for the unit.

9. The electrocautery unit of claim 8 in which the microprocessor further comprises:

a power select input including a memory register for receiving and storing power level data corresponding to a pre-determined power output level for the unit selected by the user; and a data processor, operatively connected to the power select input, to the first and second A/D converter inputs, and to the signal generator, the data processor including modulator means for changing a cautery output drive signal at the cautery drive signal output in response to changes in the power output level data and in response to changes in actual power output current and voltage signals.

* * * * *